United States Patent
Kang et al.

(10) Patent No.: US 7,660,387 B2
(45) Date of Patent: Feb. 9, 2010

(54) RADIATION IMAGING SYSTEM

(75) Inventors: Kejun Kang, Beijing (CN); Zhiqiang Chen, Beijing (CN); Yuanjing Li, Beijing (CN); Liming Wang, Beijing (CN); Yinong Liu, Beijing (CN); Shangmin Sun, Beijing (CN); Li Zhang, Beijing (CN); Yaohong Liu, Beijing (CN); Guang Yang, Beijing (CN); Qingjun Zhang, Beijing (CN); Wenguo Liu, Beijing (CN); Siyuan Liang, Beijing (CN); Zhenbin Guo, Beijing (CN); Bin Hu, Beijing (CN); Yanli Deng, Beijing (CN); Yucheng Wu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 12/165,846

(22) Filed: Jul. 1, 2008

(65) Prior Publication Data

US 2009/0010387 A1    Jan. 8, 2009

(30) Foreign Application Priority Data

Jul. 2, 2007    (CN) ..................... 2007 1 0118200

(51) Int. Cl.
G01N 23/04    (2006.01)

(52) U.S. Cl. .......................................... 378/57; 378/62

(58) Field of Classification Search .................... 378/4, 378/19, 62, 64, 57, 162, 165, 901
See application file for complete search history.

(56) References Cited

U.S. PATENT DOCUMENTS 6,335,958 B1 *    1/2002    Munier et al. ................. 378/19
2003/0128801 A1 *    7/2003    Eisenberg et al. ............. 378/19

FOREIGN PATENT DOCUMENTS

RU    2 273 844 C1    1/2006

* cited by examiner

Primary Examiner—Irakli Kiknadze
(74) Attorney, Agent, or Firm—Westman, Champlin & Kelly, P.A.

(57) ABSTRACT

The present invention discloses an radiation imaging system, comprising: an accelerator for generating rays which penetrate through the objects to be inspected and an synchronous signal; a detector with a plurality of detecting modules, adapted for detecting rays; a signal processor for generating a selection signal according to the synchronous signal, so as to select a detecting module for detecting the rays; a data converter for converting the signal detected by said detecting module into digital data, and then buffering the digital data in said signal processor; and a communication controller connected to an image processor, adapted for transmitting the digital data buffered in said signal processor to said image processor. The system according to the present invention allows high-speed and stable data acquisition and data conversion and accurate and reliable data transmission, when the data amount is significant.

9 Claims, 4 Drawing Sheets

(A)  (B)

(A)  (B)

RADIATION IMAGING SYSTEM

FIELD OF THE INVENTION

The present invention relates to a radiation imaging system, more specifically, to a radiation imaging system that can make radiation imaging for high speed cars and obtain clear images.

BACKGROUND OF THE INVENTION

The present application claims priority of Chinese patent application Serial No. 200710118200.7, filed Jul. 2, 2007, the content of which is hereby incorporated by reference in its entirety.

During scan imaging, an accelerator generates high-energy X-ray pulses, which penetrate through the object under scan. Detector arrays with high sensitivity receive the X-rays, and convert them into an electrical signal for output. Then, columns of digital images are generated in real time by an image acquisition subsystem. When the entire scanning process completes, a whole image for the scanned object will be obtained at a system control station.

In an imaging system, a main function of an accelerator is to generate X-ray pulses under control. A detector converts the X-rays penetrating through a scanned object into an analog electrical signal, and then sends the signal to an image acquisition system. The image acquisition system then converts the analog electrical signal acquired from the detector system into a digital signal. Depending on the digital signal, an image is established by an image acquisition station.

In the existing scan imaging, the scanning speed thereof should not be too fast, approximately at 4 km/h. With the increase of the inspection requirements, a system that can achieve high-speed scan imaging is urgently needed, which may be used for security inspection, for example for cars on land ports and various checkpoints without parking, or for low-speed check on trains and the like.

Particularly, how to achieve high-speed acquisition for data when a car is running very fast, such as at a speed of 30 km per hour, is a main confronted problem. There are two kinds of commonly employed data acquisition systems applied in the inspection systems for X-rays source in the same field, particularly as follows: 1) designing a dedicated transmission data bus according to the system structure; 2) transmitting data using the field bus technology. Considering the inspection system for high-speed acquisition, the design of a dedicated data transmission bus is disadvantageous for extending. When the number of detecting units is increased, the amount of data transmission on the original bus can not meet requirements, and it is needed to redesign the system. However, the field bus technology applied in the radiation inspection systems has a lower transmission rate, such as CAN bus, the highest transmission rate thereof is 1 Mbps, and can not satisfy the tasks for real-time high-speed acquisition and transmission of mass data.

SUMMARY OF THE INVENTION

An object of the present invention is to provide a high-speed radiation imaging system for performing inspections on rail vehicles, which allows high-speed stability to the collection of data and transform data, and correct and reliable transmission of data, when the inspected objects are passing through the scanning passage at high speeds. When the number of detecting units increases, it is possible to meet requirements through extending the data acquisition system.

In an aspect of the present invention, there is provided an radiation imaging system, comprising: an accelerator for generating rays which penetrate through the objects to be inspected and an synchronous signal; a detector for detecting the rays; a signal processor for generating a selection signal according to the synchronous signal, so as to select one detector for detecting the rays; a data converter for converting the signal detected by the detector into digital data, and then buffering the digital data in the signal processor; and a communication controller connected to an image processor, adapted for transmitting the digital data buffered in the signal processor to the image processor.

Preferably, the data converter and the signal processor are connected via parallel buses.

Preferably, the signal processor and the communication controller are connected via parallel buses.

Preferably, the communication controller and the image processor are connected via high-speed serial buses.

Preferably, the data acquisition system is extensible.

Preferably, the extension for the data acquisition system is implemented by extended buses of the signal processor.

Preferably, the communication controller is implemented based on a RISC processor.

Preferably, a scanning frequency of the rays is beyond 40 Hz.

Preferably, a speed of the object to be inspected is higher than 4 km/h.

Preferably, a number of the detecting units included in the detector is extensible.

According to the present invention, the speed of data acquisition of the X-ray inspection system is increased, since the extensibility thereof has broad adaptability, which may be not only adapted to the rail vehicles inspection system with such as 30 km/h or higher operating rate and greater data amount, abut also adapted to the other products in the nondestructive detection field.

BRIEF DESCRIPTION OF THE DRAWINGS

The above features, advantageous of the present invention will become more apparent from the following detail description given in conjunction with attaching drawings, in which.

DETAILED DESCRIPTION OF THE PREFERRED EMBODIMENTS

Figure 1:
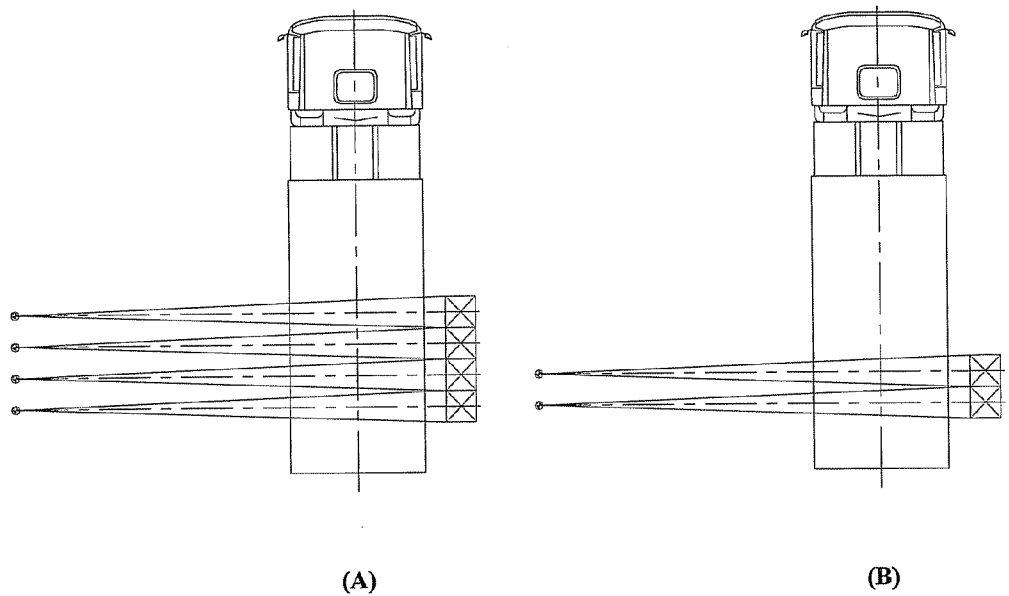
FIG. 1 is a schematic diagram for illustrating a rapid triggered scanning manner of the present invention, and a slow triggered scanning manner of the prior art.

Hereafter preferred embodiments of the present invention will be explained in detail with reference to the drawings. In the drawings, the like reference numbers refer to the same or the like components in the different drawings. For the clarify and simplicity, the detail descriptions for the already known functions and structures herein will be omitted, in order to avoid obscuring the subject matter of the present invention.

FIG. 1 is a schematic diagram for illustrating a rapid triggered scanning manner of the present invention and a slow triggered scanning manner of the prior art. As shown in (A) and (B) of FIG. 1, an accelerator generates X-rays with high frequency under control, the frequency thereof is Hundreds of Hertz per second, and It can product one column image in each pulse. Therefore, the more pulse rays there are in unit time, the more column images formed in unit time, thereby increasing the speed of the scanning imaging. That is, it is possible to increase the speed of imaging by increasing the frequency at which the accelerator generates scanning pulses.

Figure 2:
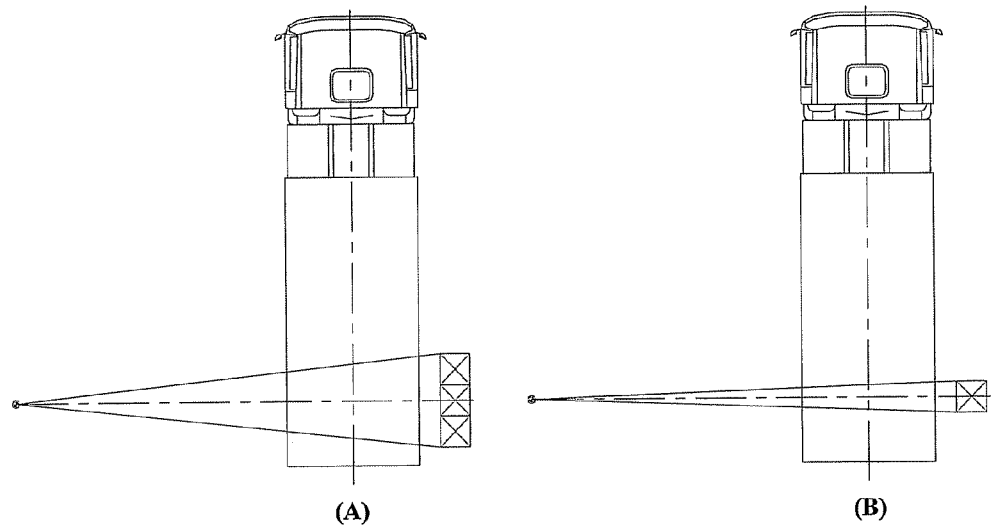
FIG. 2 is a schematic diagram for illustrating an area-doubling detector of the present invention and a conventional detector of the prior art.

FIG. 2 is a schematic diagram for illustrating an area-doubling detector of the present invention and a conventional detector of the prior art. A width of an image to which the pulse object is scanned each time is associated with the imaging area of the detector. As shown in (A) and (B) of FIG. 2, the larger the area of the detector is, the larger the area of the object that is scanned to an image each time is. If the cross-sectional area of the detector is increased, it is possible to increase the speed of scanning imaging. Therefore, if the cross-sectional area of the detector is increased, it is possible to increase the distance length of a single scanning, thereby increasing the scanning speed. That is, by use of the area-doubled detector, it is possible to obtain doubled multi-columns of data for each pulse ray, thus increasing the frequency and the speed of the scanning.

However, it is necessary to improve the existing data acquisition systems based on a single-detector or with low scanning speed, no matter for increasing the scanning speed or doubling the area of the detector, since the data amount acquired in unit time will be doubled with the increase of the imaging speed.

Currently, Ethernet communication is the most popular high-speed serial bus, which is widely applied in the computer network field and can achieve a very high communication rate. The transmission based on TCP/IP protocol may present the following advantageous, such as assuring high reliability of data, having broad technical support, and the lower cost for system development, training and maintenance. The application of the standard Ethernet technical in the industrial real-time acquisition control may account for the difficult problems in the reliable transmission for the mass of data. For the radiation imaging inspection system requiring high-speed acquisition for mass of data, it is a very suitable selection to adopt a method based on Ethernet communication to design a high-speed data acquisition system.

Figure 3:
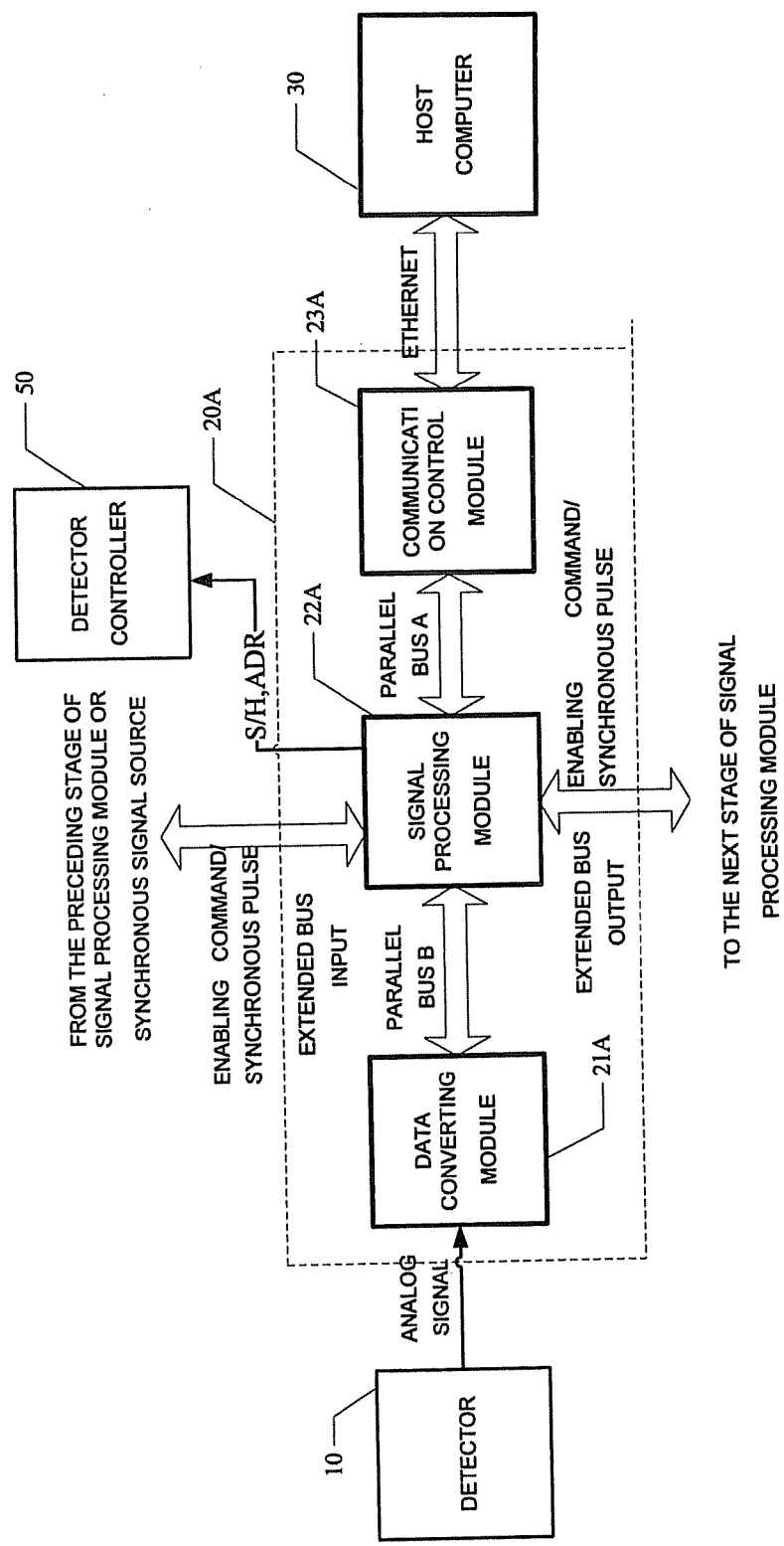
FIG. 3 is a functional block diagram of a high-speed data acquisition subsystem based on Ethernet according to an embodiment of the present invention.

FIG. 3 is a functional block diagram of a high-speed data acquisition system based on Ethernet according to an embodiment of the present invention.

As shown in FIG. 3, the high-speed data acquisition system according to the embodiment of the present invention comprises a detector 10 with a plurality of detecting modules, a data acquisition part 20A, a host computer 30, a synchronous signal source 40 and a detector controller 50. The data acquisition part 20A comprises a data converting module 21A connected to the detector 10, a signal processing module 22A connected to the data converting module 21A via a parallel bus B, a communication control module 23A connected to the signal processing module 22A via a parallel bus A. Also, the communication control module 23A is connected to the host computer 30 via an Ethernet connection.

An analog signal generated by the detector 10 is input into the data converting module 21A, which mainly implements the conversion function from an analog signal to a digital signal. According to the embodiment of the present invention, the operation of the data converting module is under control of the signal processing module. The data converting module carries out A/D conversion on the data from the detector in time-sharing manner, sends the resulting digital data to the signal processing module 22A, and then the data is buffered in the signal processing module 22A.

The operation of the data buffering is under control of the signal processing module 22A, since there are several data converting modules in the system, the signal processing module 22A sends an addressing signal to the data converting module 21A via the address bus of the parallel bus B. The data converting module 21A compares the received address signal, and confirms whether the signal is selected. When it is confirmed that the signal is selected, the data converting module 21A sends a strobe signal and occupies the data bus of the parallel bus B, and sends the converted data in turn into the data processing module 22A.

The main functions of the signal processing module 22A are as follows: accepting various control commands and operating parameters from the host computer 30, configuring the operating parameters of the system according to the commands from the host computer 30 and executing the corresponding operations, controlling the data converting module 21A to carry out A/D conversion, data buffering and transmission, and controlling the other modules to operate synchronously based on the same acquisition frequency, meanwhile achieving the extensible functions of the high-speed data acquisition system via the extended buses.

The operating process of the signal processing module 22A comprises two parts, one is to configure parameters, in which before the data acquisition, the host computer 30 communicates with the communication control module 23A over Ethernet, and carries out the parameters configuration for the signal processing module 22A via the parallel bus A. The other part is the data acquisition, in which after the parameters configuration, the data acquisition is started once receiving a control enabling command for enabling the data acquisition, and the acquisition is stopped once the command is stopped. The signal processing module 22A outputs an acquisition-holding signal and an address selection signal to the detector, so that the detector may hold the signal when the output analog signal achieves its peak value, and after the signal holding, the signal processing module 22A may select the signal of the specified detector based on the address selection signal for output to the data converting module 21A.

The above steps are repeated, until the control process from the data converting to the data buffering is completed. Then, a data ready signal is send to the communication control module 23A via the parallel bus A, in order to request for transmitting data to the host computer 30 through the communication control module 23A.

Figure 4:
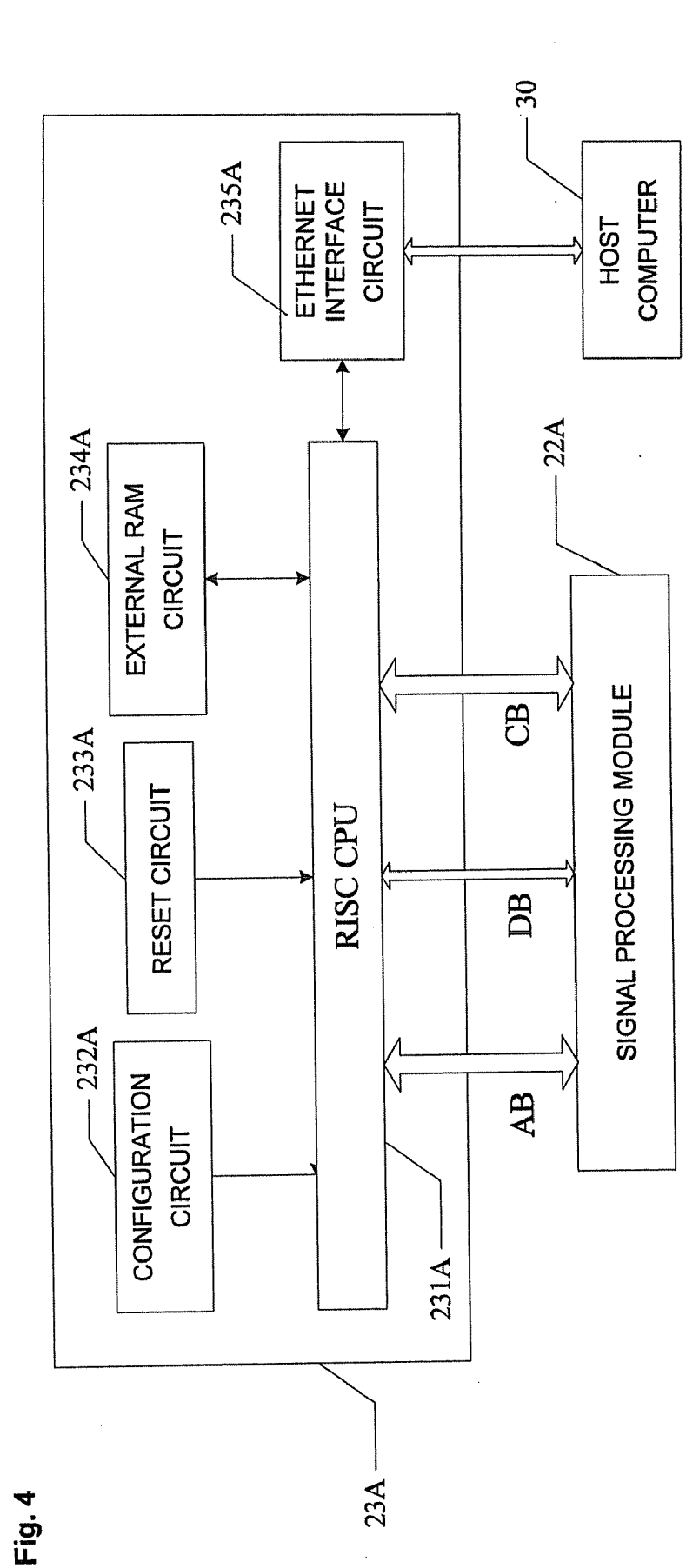
FIG. 4 is a detailed structural block diagram of the Ethernet module shown in FIG. 3.

FIG. 4 is a detailed structural block diagram of the communication control module shown in FIG. 3. As shown is FIG. 4, the communication control module 23A is based on a RISC processor 231A of Ubicom Inc., and communicates with the host computer 30 based on the TCP/IP protocol. The communication control module 23A receives a command sent from the host computer 30 and performs the corresponding operations. Meanwhile, the communication control module 23A responds to an interrupt signal sent from the signal processing module 22A, and sends the acquired data in the format based on the TCP/IP protocol to the host computer 30. The data format and the control command during the communication are promised beforehand based on the TCP/IP protocol. A communication fault-tolerance mechanism is regulated, so as to assure reliable data transmission.

The RISC processor 231A adopts IP2022-120 with a speed up to 120 MIPS, a duplex communication module in-chip may adopt software to implement various general communication interfaces. A configuration circuit 242A is used to set configuration information of the communication control module 23A, such as IP addresses, protocol types and the like. An external RAM circuit 234A is used to extend memory space of the system, such as protocol stack and the like. The communication control module 23A is connected to the host computer 30 over Ethernet. An Ethernet interface circuit 245A is used to drive and isolate the transmitted signals. The communication control module 23A is connected to the signal processing module 22A in a parallel bus manner. The host computer 30 communicates with the communication control module 23A in a server/client manner, in which the host computer 30 acts as a server, whereas the communication control module 23A acts as a client, the both above adopt the strict TCP/IP communication interface protocols to assure the communication reliability and promise the handling mechanisms for abnormities during the communication. When the communication control module 23A is powered on or reset, it initiatively sends a connection request to the host computer 30. When there are abnormities in the network, the communication control module 23A will initiatively disconnection from the network of the host computer 30, and will automatically reset through a reset circuit 233A.

Figure 5:
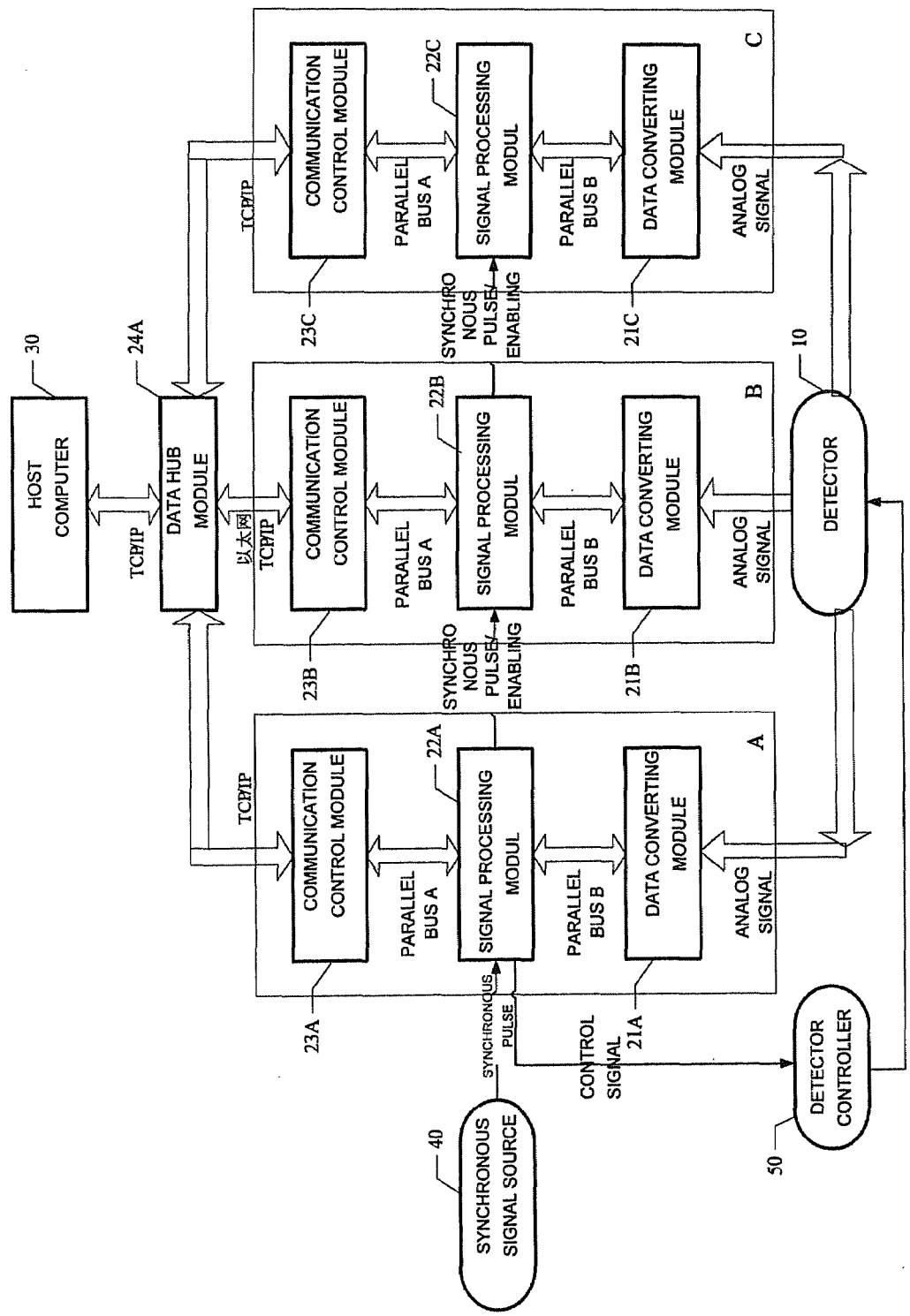
FIG. 5 is a block diagram of the high-speed data acquisition subsystem for use in the rail vehicles inspection system according to an embodiment of the present invention.

FIG. 5 is a block diagram of the high-speed data acquisition system according to the embodiment of the present invention. As shown in FIG. 5, the high-speed data acquisition system shown in FIG. 3 may be extended to meet the requirements for the higher-speed data acquisition. For example, in this inspection system, the high-speed acquisition requirement is met by extending three above data acquisition systems. The operating synchronizations between the respective units are assured by the signal processing module 22A using an acquisition-enabling signal and synchronization pulses passed through the extended bus.

As shown in FIG. 5, when the signal processing module 22A sends a command to select one detector, it sends a synchronous pulse/enabling signal to the signal processing module 22B at the same time. In this case, an analog signal output by the detector is input into the data converting module 21B. The data converting module 21B will convert the input analog signal into digital data, and buffer the data in the RAM of the data processing module 22B, The communication control module 23B establishes a connection with the host computer 30 through an exchanger 60, after which the operating states of the communication control module 23B is under control of the host computer 30, and the communication control module 23B will transmit the acquired digital data to the host computer in real time, after completing one acquisition conversion.

Similarly, when the signal processing module 22A sends a command to select one detector, it sends a synchronous pulse/enabling signal to the signal processing module 22C at the same time. In this case, an analog signal output by the detector is input into the data converting module 21C. The data converting module 21C will convert the input analog signal into digital data, and buffer the data in the RAM of the data processing module 22C. The communication control module 23C establishes a connection with the host computer 30 through an exchanger 60, after which the communication control module 23C will transmit the acquired digital data to the host computer in real time, after completing one acquisition conversion.

According to the embodiment of the present invention, such data acquisition units may be extended on demand. The data acquisition units have very good compatibility and applicability for the high-speed acquisition of the mass of data. It is possible to expediently and rapidly achieve the system requirements by extending the acquisition units.

The foregoing description gives only the preferred embodiments of the present invention. Thus, the ordinary skilled in the prior art will appreciate that, any modification, or local substitution made within the scope of the present invention should belong to the scope defined in the claims of the present invention. Accordingly, the protection scope of the present invention should depend on the protection scope of the claims.

What is claimed is:

1. A radiation imaging system, comprising:
   an accelerator for generating rays which penetrate through the object to be inspected and an synchronous signal;
   a detector comprising at least one detecting unit for detecting the rays; and
   a data acquisition system comprising:
      a signal processor for generating a selection signal according to the synchronous signal, so as to select one detector for detecting the rays;
      a data converter for converting the signal detected by said detector into digital data, and then buffering the digital data in said signal processor; and
      a communication controller connected to an image processor, adapted for transmitting the digital data buffering in said signal processor to said image processor;
   wherein the number of detecting units included in said detector is extensible.

2. The radiation imaging system according to claim 1, characterized in that, said data convertor and said signal processor are connected via parallel buses.

3. The radiation imaging system according to claim 1, characterized in that, said signal processor and said communication controller are connected via parallel buses.

4. The radiation imaging system according to claim 1, characterized in that, said communication controller and said image processor are connected via high-speed serial buses.

5. The radiation imaging system according to claim 1, characterized in that, said data acquisition is extensible.

6. The radiation imaging system according to claim 5, characterized in that, the extension for said data acquisition system is implemented by extended buses of said signal processor.

7. The radiation imaging system according to claim 1, characterized in that, said communication controller is implemented based on an RISC processor.

8. The radiation imaging system according to claim 1, characterized in that, a scanning frequency of the rays is beyond 40 Hz.

9. The radiation imaging system according to claim 1, characterized in that, a speed of said object to be inspected is higher than 4 km/h.

* * * * *